United States Patent [19]

Schnalke et al.

[11] Patent Number: 5,350,865

[45] Date of Patent: Sep. 27, 1994

[54] PROCESS FOR THE PREPARATION OF DIFLUOROBENZODIOXOLE AND CHLOROFLUOROBENZODIOXOLE

[75] Inventors: Karl-Erwin Schnalke, Leverkusen; Josef Heinrich, Solingen-Wald; Fritz Döring, Odenthal-Gloebusch, all of Fed. Rep. of Germany

[73] Assignee: Bayer Aktiengesellschaft, Leverkusen, Fed. Rep. of Germany

[21] Appl. No.: 126,823

[22] Filed: Sep. 24, 1993

[30] Foreign Application Priority Data

Oct. 2, 1992 [DE] Fed. Rep. of Germany ....... 4233199

[51] Int. Cl.$^5$ ............................................ C07D 317/46
[52] U.S. Cl. .................................................... 549/434
[58] Field of Search ......................................... 549/434

[56] References Cited

U.S. PATENT DOCUMENTS

| | | | |
|---|---|---|---|
| 4,110,345 | 8/1978 | Berkelhammer et al. | 549/434 |
| 4,284,643 | 8/1981 | Fuchs et al. | 424/282 |
| 4,310,540 | 1/1982 | Lantzsch et al. | 424/282 |
| 4,438,275 | 3/1984 | Lantzsch et al. | 549/434 |
| 4,600,787 | 7/1986 | Marhold et al. | 549/434 |
| 5,106,867 | 4/1992 | Bloom et al. | 549/434 |
| 5,258,526 | 11/1993 | Knuppel et al. | 548/526 |
| 5,260,460 | 11/1993 | Andres et al. | 549/434 |
| 5,281,725 | 1/1994 | Andres et al. | 549/434 |

FOREIGN PATENT DOCUMENTS

| | | |
|---|---|---|
| 041131 | 4/1979 | European Pat. Off. . |
| 008732 | 8/1979 | European Pat. Off. . |
| 0423009 | 4/1991 | European Pat. Off. . |
| 3315147 | 10/1984 | Fed. Rep. of Germany . |
| 3642256 | 6/1987 | Fed. Rep. of Germany . |
| 0333661 | 9/1989 | Fed. Rep. of Germany . |

*Primary Examiner*—C. Warren Ivy
*Assistant Examiner*—A. A. Owens
*Attorney, Agent, or Firm*—Sprung Horn Kramer & Woods

[57] ABSTRACT

A novel process for the preparation of benzodioxoles of the formula (I)

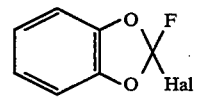

(I)

in which
Hal represents a chlorine atom or a fluorine atom, from dichlorobenzodioxole using stoichiometric quantities of anhydrous hydrofluoric acid.

3 Claims, No Drawings

PROCESS FOR THE PREPARATION OF DIFLUOROBENZODIOXOLE AND CHLOROFLUOROBENZODIOXOLE

The present invention relates to a novel process for preparing the known difluorobenzodioxole and chlorofluorobenzodioxole, which can be used as intermediates for the synthesis of highly active compounds in a wide variety of areas, e.g. for the synthesis of active compounds having fungicidal properties, suitable for use in plant protection.

It is already known that difluorobenzodioxole can be prepared from the dichloro compound using potassium fluoride in the presence of a catalyst and optionally in the presence of a solvent (cf. EP 0 423009). In addition, the synthesis is known of aromatic compounds possessing perfluorinated side chains whose fluorination is carried out using potassium fluoride in the presence of Lewis acids (cf. DE 3 315 147). Fluorine-substituted benzodioxoles can also be prepared from the corresponding dichloro compounds using ammonium fluorides or alkali metal fluorides in the presence of a catalyst and in the presence of a solvent (cf. DE 3 642 256).

There are some disadvantages attached to all these processes. The solid fluorinations with alkali metal fluorides make use of solvents, as a result of which the space time yield is low; furthermore, the recovery of the solvents is very complex, and disposal problems arise in association with the large quantities of alkali metal chlorides.

In addition, a process is known which makes use of hydrofluoric acid. A large excess of anhydrous hydrofluoric acid is initially introduced, and the dichlorobenzodioxole is added dropwise (cf. EP 41131). Although this reaction proceeds smoothly, the product is partially destroyed once more as a result of the thermal stress associated with recovery by distillation of the excess hydrofluoric acid. Besides this, in connection with the purification by distillation of the product itself, there are substantial problems with high-boiling by-products, which eliminate hydrogen fluoride and lead to a discoloration of the product. In addition, the yield is naturally reduced, and amounts to between 68 to 78% of theory.

It has now been found that the known benzodioxoles of the formula ( I )

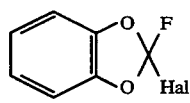

in which
Hal represents chlorine or fluorine, are obtained if dichlorobenzodioxole of the formula (II)

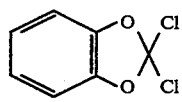

is initially introduced and stoichiometric quantities (1 or 2 mol) of anhydrous hydrofluoric acid are metered in at temperatures between −20° and room temperature and a pressure of between 0 and 25 bar.

It is to be considered extremely surprising that the benzodioxoles of the formula (I) can be prepared by the process according to the invention in extremely high yield and with exceptional purity. Thus, on the basis of the known state of the art, it could not have been supposed that the use of only stoichiometric quantities of anhydrous hydrofluoric acid can produce the desired benzodioxoles with such a high selectivity and that, in addition, the fluorination can be halted at the stage of the chlorofluorobenzodioxole, and affords such good yields as well.

The process according to the invention is distinguished by a number of advantages. Thus, it permits, as already mentioned, the preparation of difluorobenzodioxole in extremely high yield and with exceptional purity, as well as that of chlorofluorobenzodioxole in good yields.

In this connection, it is particularly advantageous that, as a result of the stoichiometric use of the anhydrous hydrofluoric acid, the complicated recovery of hydrofluoric acid is dispensed with, and a very high space-time yield is achieved. As a result of the high degree of selectivity, the working up of the product likewise becomes very simple, since hardly any residues arise which have to be disposed of.

This is therefore a process which can also be carried out in a trouble-free manner on an industrial scale, and which produces the compounds in high yield and with great purity under these conditions as well, and in association with which there is little environmental pollution due to distillation residues and organically contaminated salt residues.

If dichlorobenzodioxole is reacted with 1 or 2 mol, respectively, of anhydrous hydrofluoric acid, the course of the process according to the invention can then be visualised by the following formula diagram:

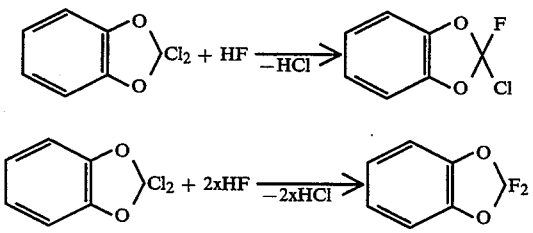

The dichlorobenzodioxole which is required as a starting material in carrying out the process according to the invention is known and can be prepared by known processes (cf. US 4 438 275 and the references in column 15, H. Gross-Monatsberichte Deutsch. Akad. Wiss. Berlin 6(5), 356-362 (1964)). Thus, it can be prepared from benzodioxole (cf. J. Chem. Soc. 93, 566 (1988)), or from the corresponding pyrocatechol carbonate (Chem. Ber. 96, 1382 (1963)) or the corresponding pyrocatechol orthoformate (Chem. Ber. 94, 544 (1961)) by reaction with phosphorus pentachloride. The benzodioxole which is to be employed in this connection is commercially available.

In carrying out the process according to the invention, the dichlorobenzodioxole is initially introduced and the anhydrous hydrofluoric acid is metered in under nitrogen within the space of 4 hours, the discharge of the hydrogen chloride gas being the reaction-determining step. After a certain subsequent reaction time, the reaction mixture is worked up by distillation in vacuo. In the course of the process, the reaction can be halted at the stage of the chlorofluorobenzodioxole, and the latter can be removed by distillation.

In carrying out the process according to the invention, the reaction temperature can be varied within a particular range. In general, temperatures of between −20° C. and room temperature, preferably of between −10° C. and room temperature, are employed. In general, the reaction is started at 0° C., at which temperature the starting material is still liquid, and is only cooled to the indicated temperatures during the course of the reaction in order to keep the reaction mixture liquid.

The benzodioxoles of the formula (I) are valuable precursors for the preparation of highly active compounds which are employed, inter alia, in plant protection, e.g. for combating fungi (cf. DE-A 4 107 398 and EPO 333661). Starting from difluorobenzodioxole, the compound which is either brominated or metallated in the 4-position is prepared, and this is then reacted with acrylonitrile to give the corresponding acrylonitrile derivative which is then further reacted with phenylsulfonylmethyl isocyanide to give a highly active 4-cyanopyrrole derivative. If the route by way of the 4-bromo compound is selected, the course of the reaction can then be represented by the following formula diagrams:

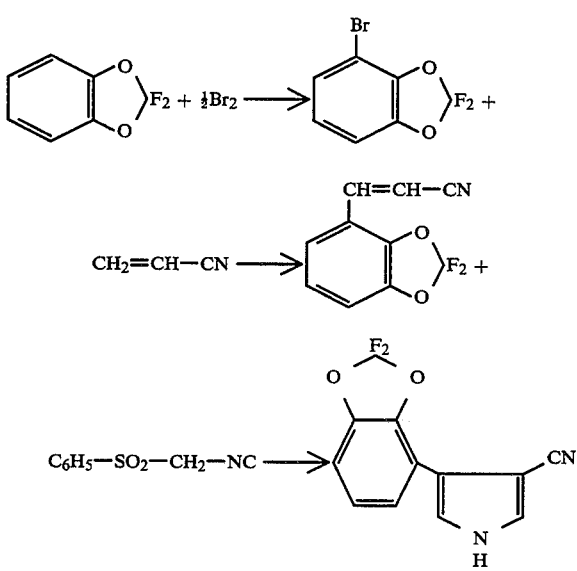

PREPARATION EXAMPLES

EXAMPLE 1

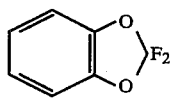

11 kg of dichlorobenzodioxole (content 92%) are initially introduced at −0° C. into a fluorination apparatus comprising a 15 l reactor, a 2 m-long column (diameter 50 mm) filled with 6 mm stainless-steel packing material and pressure receivers. The pressure release of the system is adjusted to 6 bar. 5 bar of nitrogen are injected. 2200 g of anhydrous hydrofluoric acid are metered in by way of a metering pump at a temperature of 0° C. to −10° C. within the space of 4 hours. The resulting hydrogen chloride off-gas is released continuously at a pressure of 6 bar. The mixture is subsequently stirred for one hour, in association with which the temperature is raised to 10° C. Subsequently, the pressure in the system is released down to 1 bar within the space of one hour.

The reaction mixture is distilled in vacuo. A weight of 7900 g with a content of 99.3% is obtained under 12 mbar and at 32° to 34° C. This corresponds to a yield of 93,7% of theory.

EXAMPLE 2

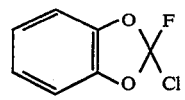

11 kg of dichlorobenzodioxole (92% strength) are initially introduced into the apparatus and under the process conditions indicated in Example 1.

1240 g of anhydrous hydrofluoric acid are metered in at 0° C. to −10° C. within the space of 4 hours.

After subsequently stirring the mixture for a further 0.5 hour, the pressure in the system is released and the reaction mixture is worked up by distillation.

Fraction 1 b.p. 32° to 36° C. 15 mbar 1490 g
Fraction 2 b.p. 36° to 56° C. 15 mbar 274 g
Fraction 3 b.p. 56° to 58° C. 15 mbar 6846 g Composition of the individual fractions:

| Fraction | Difluorobenzodioxole in % | Chlorofluorobenzodioxole in % |
| --- | --- | --- |
| 1 | 99.6 | 0.2 |
| 2 | 42.1 | 55.4 |
| 3 | — | 97.0 |

This results in a yield of 73.4% of chlorofluorobenzodioxole with a purity of >95%.

What is claimed is:

1. A process for the preparation of a benzodioxole of the formula ( I )

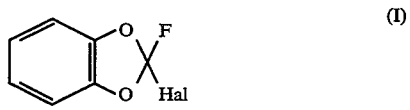

in which
Hal is a chlorine atom or a fluorine atom, which comprises metering into a dichlorobenzodioxole of the formula (II)

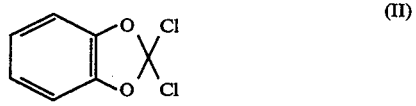

a stoichiometric quantity of anhydrous hydrofluoric acid at a temperature between −10° and room temperature and under pressure of between 1 and 10 bar.

2. A process according to claim 1, wherein 2 mols of anhydrous hydrofluoric acid are employed per mol of dichlorobenzodioxole.

3. A process according to claim 1, wherein 1 mol of anhydrous hydrofluoric acid is employed per mol of dichlorobenzodioxole.

* * * * *